United States Patent [19]

Metcalf et al.

[11] 4,289,762
[45] Sep. 15, 1981

[54] 10-(1,2-PROPADIENYL) STEROIDS AS IRREVERSIBLE AROMATASE INHIBITORS

[75] Inventors: Brian W. Metcalf, Mason; J. O'Neal Johnston, Cincinnati, both of Ohio

[73] Assignee: Merrell Dow Pharmaceuticals Inc., Cincinnati, Ohio

[21] Appl. No.: 163,453

[22] Filed: Jun. 27, 1980

[51] Int. Cl.³ .................. A61K 31/56; A61K 31/58
[52] U.S. Cl. .................. 424/242; 424/241; 424/243; 260/239.55 R; 260/239.55 C; 260/397.3; 260/397.5; 260/397.4
[58] Field of Search .................. 260/397.4; 424/243, 424/241, 242

[56] References Cited

U.S. PATENT DOCUMENTS 3,939,264  2/1976  Lachnit-Fixson .................. 260/397.4
4,052,421 10/1977  Biollaz et al. .................. 260/397.4

Primary Examiner—Elbert L. Roberts
Attorney, Agent, or Firm—John J. Kolano; Raymond A. McDonald; William J. Stein

[57] ABSTRACT

Irreversible aromatase inhibitors are provided having the formulae

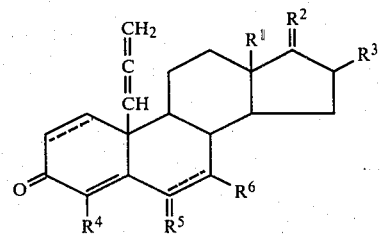

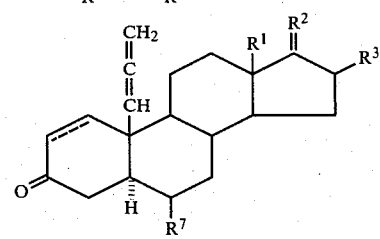

wherein ≡:
represents a single or a double bond; $R^1$ is $CH_3$ or $C_2H_5$; $R^2$ is (H) ($OR^8$) or O; $R^3$ is H or $C_{1-3}$ alkyl; $R^4$ is H or $OR^8$; $R^5$ is $H_2$, O or (H) ($C_{1-3}$ alkyl); $R^6$ and $R^7$ are each independently H or $C_{1-3}$ alkyl; and $R^8$ is H or $C_{1-4}$ alkanoyl. Intermediates useful in preparing the foregoing aromatase inhibitors, methods of using them and a pharmaceutical composition containing them are also provided.

23 Claims, No Drawings

10-(1,2-PROPADIENYL) STEROIDS AS IRREVERSIBLE AROMATASE INHIBITORS

BACKGROUND OF THE INVENTION

This invention relates to 10-(1,2-propadienyl) steroids which are irreversible inhibitors of aromatase enzymes. Processes for preparing these steroids and methods of using them are also provided.

Divergent sex hormones which are synthesized by the gonads and, to a lesser extent, by the adrenals, are primarily responsible for the expression of secondary sex characteristics of either males or females. These steroids are regulated by a number of enzymes. The enzyme aromatase is the rate-limiting enzyme in the conversion of androgens (male hormones) to estrogens (female hormones). The non-reversible conversion of androgens to estrogens involves the oxidation and elimination of the methyl group from C10 as formic acid. The $1\beta$ and $2\beta$ hydrogens from C1 and C2 are also lost to produce the aromatic A-ring of estrogens. The androgens, testosterone and androstenedione, or the estrogens, estradiol and estrone, can be interconverted by $17\beta$-hydroxy-steroid dehydrogenase (FIG. 1). The regulation of the conversion of androgen to estrogen or the inhibition of this conversion has therapeutic utility in regulating clinical conditions which are potentiated by the presence of estrogens.

There is substantial clinical evidence that many tumor types are associated with elevated estrogen production. Ovariectomy, adrenalectomy and hypophysectomy are commonly employed in patients with breast cancer as a means of reducing the amount of estrogen. Non-surgical procedures include treatments with high levels of steroids, anti-estrogens and inhibitors of steroidal enzymatic pathways. Treatment with anti-estrogens results in about one-third of the patients obtaining objective tumor regressions. Adrenalectomy will cause regression of breast cancer in postmenopausal women with hormonal-dependent tumors, presumably as the result of reduction in available estrogen derived from androstenedione, whose source is primarily from the adrenals. Growth of several lines of breast cancer cells have been shown to be estrogen-dependent, and can be inhibited by compounds which antagonize estrogen action.

Inhibitors of estrogen biosynthesis have been identified using microsomal enzyme preparations from human placenta. Aromatase inhibitors such as 4-hydroxy- and 4-acetoxy-androstene-3,17-dione, aminoglutethimide and testololactone are capable of blocking the aromatization of androgens to estrogens and can effectively prevent the biologically active estrogens from reaching endocrine tumors or reduce estrogen biosynthesis in those tumors capable of endogenous estrogen synthesis, thereby producing remissions of metastatic breast cancer.

Endometrial cancer has been related to the presence of excessive endogenous or exogenous estrogen. Gonadal and trophoblastic tumors cause somatic hyperestrogenization, which results in varying degrees of feminization in males. In females, the symptoms depend upon the age of the patient, and may range from precocious pseudopuberty to abnormalities of menses to postmenopausal bleeding. Aromatase inhibitors can be used in adjunctive therapy in the conservative management of patients with such tumors, since they will reduce the somatic expression of increased estrogen biosynthesis. Aromatase inhibitors have been administered for treatment of hyperestrogenemia in conditions such as gynecomastia, and have resulted in clinical improvement.

Hyperestrogenemia has been suggested to precede myocardial infarction. Reduction in peripheral aromatization of androgens by administration of aromatase inhibitors could therefore be useful for treatment of

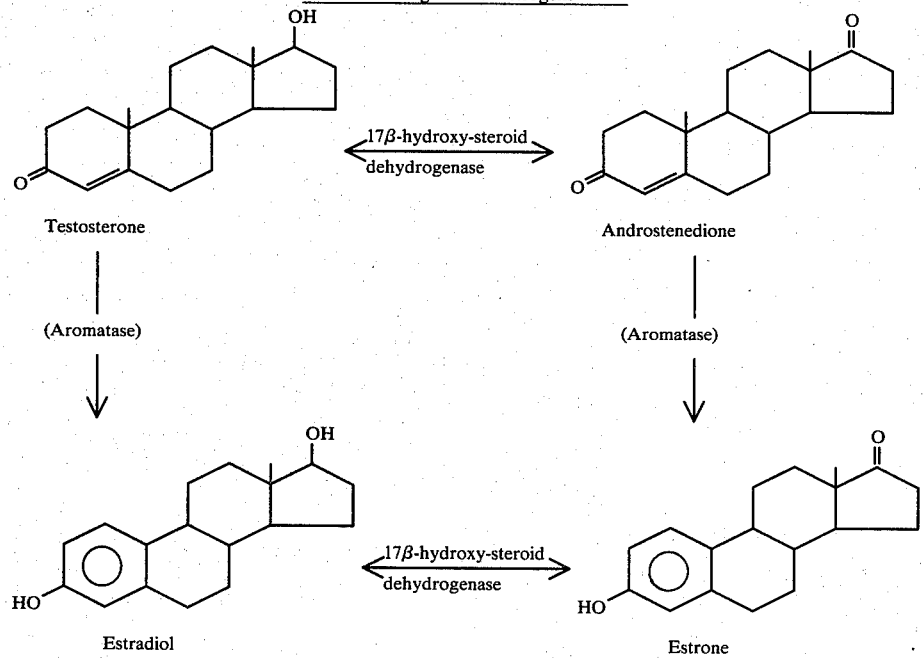

Formula 1. Enzymatic Interconversion of Androgens and Estrogens individuals having a high potential risk of myocardial infarctions.

Aromatase inhibitors have been shown to be effective in treating male infertility, and in preventing estrogen production required for ovulation in females. Since estrogen synthesis is required for implantation of fertilized ova in many species, post-coital administration of aromatase inhibitors has the potential to regulate fertility, particularly in domestic pets and wildlife. In particular, suppression of both male and female rodent reproduction could be effected during controlled mating programs using aromatase inhibitors.

SUMMARY OF THE INVENTION

The 10-(1,2-propadienyl) steroid aromatase inhibitors of the invention have the formulae

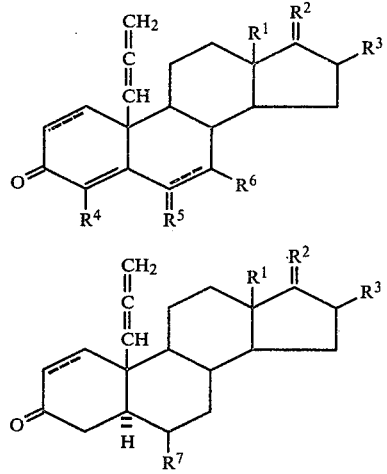

wherein ---
represents a single or a double bond; $R^1$ is $CH_3$ or $C_2H_5$; $R^2$ is (H) ($OR^8$) or O; $R^3$ is H or $C_{1-3}$ alkyl; $R^4$ is H or $OR^8$; $R^5$ is $H_2$, O or (H) ($C_{1-3}$ alkyl); $R^6$ and $R^7$ are independently H or $C_{1-3}$ alkyl; and $R^8$ is H or $C_{1-4}$ alkanoyl.

The invention further includes novel intermediates useful for the preparation of the aromatase inhibitors, and having the formulae

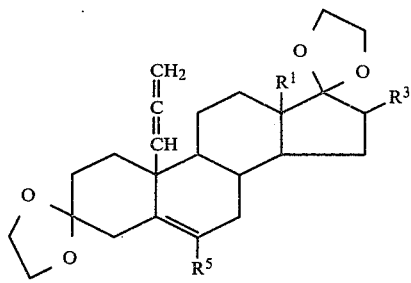

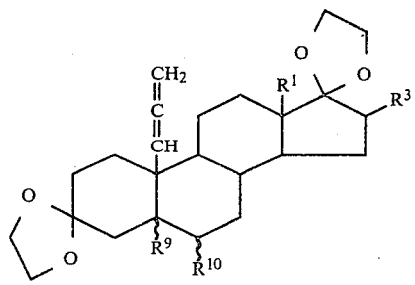

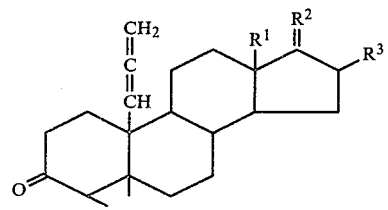

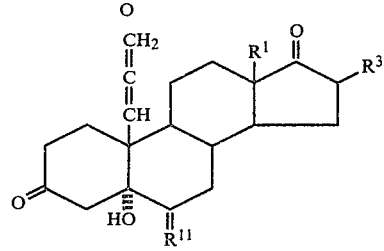

wherein $R^1$ is $CH_3$ or $C_2H_5$, $R^2$ is (H) ($OR^8$) or O; $R^3$ is H or $C_{1-3}$ alkyl; $R^5$ is H or $C_{1-3}$ alkyl; $R^8$ is H or $C_{1-4}$ alkanoyl; $R^9$ and $R^{10}$ together are >O, or $R^9$ is OH and $R^{10}$ is $C_{1-3}$ alkyl; and $R^{11}$ is (H) (OH) or O.

Methods of preparing and using the compounds of the invention are also included within the scope of the invention.

DETAILED DESCRIPTION OF THE INVENTION

The aromatase inhibitors of the invention all have in common the unusual feature of a 10-allenyl substituent. (The terms "allenyl", "propadienyl" and "1,2-propadienyl" are used interchangeably herein.) Preferably, $R^1$ is $CH_3$, and the compounds belong to the 10-(1,2-propadienyl)estrane series. The compounds either have a 4,5-double bond, as shown in Formula I, or a 5α-hydrogen, as shown in Formula II. The compounds of Formula I may also have a 1,2-double bond and/or a 6,7-double bond. The compounds of Formula II may also have a 1,2-double bond.

The substituent $R^2$ is preferably a keto group or a hydroxy, preferably a β-hydroxy group. $R^3$ may be methyl, ethyl, or propyl, but preferably is a hydrogen atom. $R^4$ is a hydroxy or an alkanoyloxy group, the alkanoyloxy being preferably acetoxy. $R^5$ is preferably hydrogen, or a keto group. $R^6$ and $R^7$ are each preferably a hydrogen atom.

The compounds according to the invention are optically active and possess the same stereochemistry at the ring junctions as the natural androstane series. Thus, the 10-allenyl group has the β-configuration, as do the axial hydrogen at C8 and the alkyl substituents at C13. In the compounds of Formulae I and II, the B/C and C/D ring junctions are trans, and the A/B ring junction is also trans in the compounds of Formula II. While the compounds having the natural steroid configuration are believed to be the active inhibitors, mixtures of those compounds with their optical antipodes are also included within the scope of the invention.

Specific and representative compounds according to the invention, in addition to those shown in the examples below, include but are not limited to the following: 7α-methyl-10-(1,2-propadienyl)estr-4-ene-3,17-dione; 6α,18-dimethyl-10-(1,2-propadienyl)estra-1,4-diene-3,17-dione; 4,17β-dihydroxy-16β-methyl-10-(1,2-propadienyl)estra-4,6-diene-3-one; 10-(1,2-propadienyl)estra-1,4-diene-3,6,17-trione; 17β-acetoxy-6β,16α-dimethyl-10-(1,2-propadienyl)-5α-estran-3-one; 18-methyl-10-(1,2-propadienyl)-5α-estr-1-ene-3,17-dione; 17β-hydroxy-10-(1,2-propadienyl)estra-1,4-dien-3-one; and 4-acetoxy-17β-hydroxy-10-(1,2-propadienyl)estr-4-en-3-one.

Compounds according to the invention having the Formulae I and II may be synthesized from known steroid precursors, either steroids derived from natural sources or from synthetic or semi-synthetic steroids. The following syntheses are illustrative for compounds of the estradione series. Analogous reactions may be effected with the 18-methyl, 6-alkyl, 7-alkyl and/or 16-alkyl series.

In each Scheme, where intermediate compounds do not undergo changes in rings C and D or in rings A, B and C, the conventional abbreviated notation is used and the omitted portion is assumed to remain unchanged.

Two different methods of introducing a 10-(1,2-propadienyl) group are illustrated below. The starting material in each case is the known diketal derived from ketalization of 19-acetoxy-androst-4-ene-3,17-dione with ethylene glycol, the double bond migrating in a known fashion to the 5,6-position, followed by hydrolysis of the acetate and oxidation of the 19-alcohol to an aldehyde.

The known aldehyde diketal 1 is further elaborated according to Scheme 1.

SCHEME 1

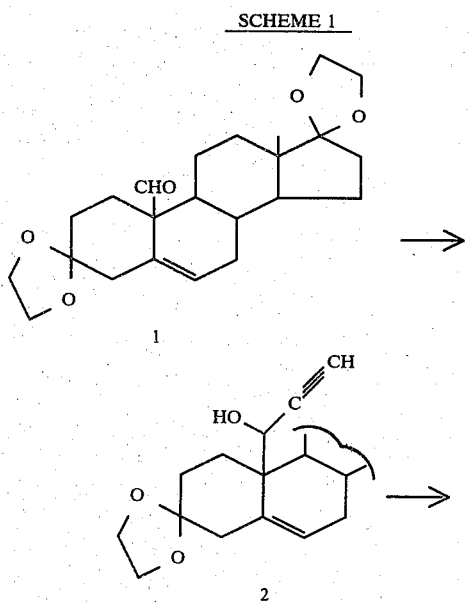

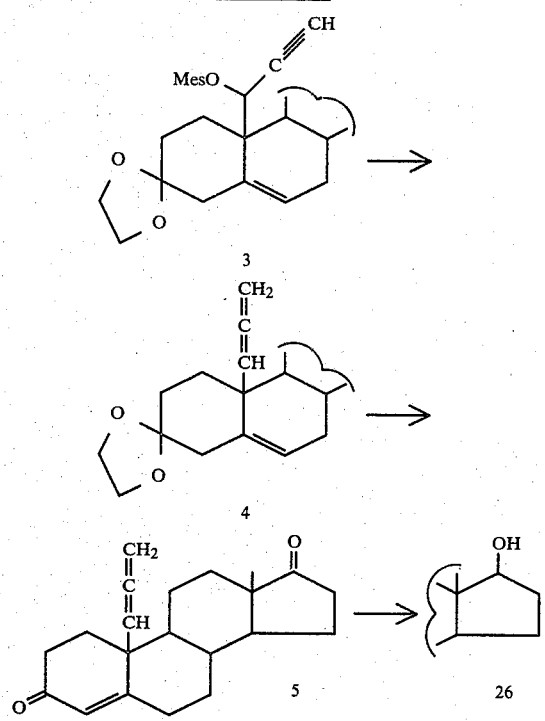

The aldehyde diketal 1 is treated with an acetylenic Grignard reagent in ether or tetrahydrofuran (THF), at 25°–45° C. for 1–10 hours. The reaction is worked up in the usual fashion, and the acetylenic alcohol 2 is obtained, according to the procedure of Covey et al, Tet. Let., 2105 (1979). The alcohol is converted to the methanesulfonate ester (mesylate) by reaction with methanesulfonyl chloride in pyridine, at −20°–0° C. for 12–48 hours. The mesylate 3 is treated with a hydride reducing agent at −70°––20° C. for 12–48 hours, according to the procedure of Stork et al, J. Am. Chem. Soc., 101, 7107 (1979), to form the propadiene 4. Deketalization with p-toluenesulfonic acid in acetone at about 25° C. for 1–24 hours, or HCl in aqueous alcohol, with concomitant conjugation of the double bond, yields the 10-(1,2-propadienyl)-4-ene-3,17-dione 5.

Preferably, the acetylenic alcohol 2 is converted to the propadiene as shown in Scheme 2.

SCHEME 2

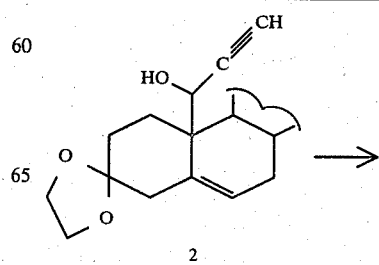

-continued
SCHEME 2

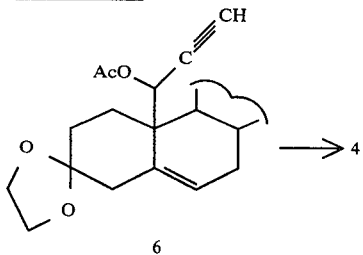

The acetylenic alcohol 2 is converted to the acetate 6 with acetic anhydride in pyridine at 25° C. for 4–20 hours. Treatment with a lithium alkynyl-alkylcopper or lithium dimethylcopper at −70° C. for 0.1–4 hours, according to the method of Baret et al., *Tetrahedron*, 35,2931 (1979), produces the propadiene 4, which is then deketalized according to the procedure of Scheme 1.

The 10-allenyl diketone 5 may be converted to the 17β-alcohol 26 by reduction with sodium borohydride in ethanol at 0° C. for 1 hour, according to the procedure of Norymberski et al, *J. Chem. Soc.*, 3426 (1955). The alcohol may be esterified with a lower akanoyl chloride in pyridine at 0°–25° C. for 1–24 hours.

Either the 10-allenyl diketone 5 or the corresponding 17-alcohol 26 may be dehydrogenated as shown in Scheme 3.

SCHEME 3

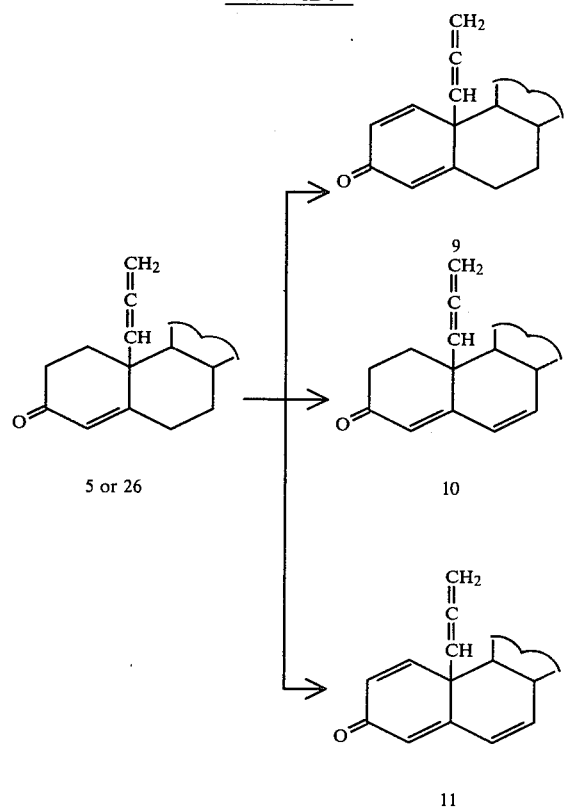

The diketone 5 or the corresponding 17-alcohol 26 is reacted with dichlorodicyanoquinone in refluxing dioxane for two hours, according to the procedure of Burn et al, *J. Chem. Soc.*, 1223 (1962) to introduce a 1,2-double bond to produce compound 9. Alternatively, the double bond in this position may be introduced by treatment of compound 5 with selenium dioxide in refluxing t-butyl alcohol for 20 hours, according to the procedure of Bernstein et al, *J. Am. Chem. Soc.*, 82, 1235 (1960).

A 6,7-double bond may be introduced by reaction of compound 5 or the corresponding 17-alcohol 26 with chloranil in refluxing t-butyl alcohol for 3 hours, according to the procedure of Agnello et al, *J. Am. Chem. Soc.*, 82, 4293 (1960), resulting in compound 10.

Both a 1,2-double bond and a 6,7-double bond may be introduced simultaneously by reaction of compound 5 or the corresponding 17-alcohol 26 with chloranil in refluxing sec-amyl alcohol for 3 hours, according to the procedure of Agnello et al, ibid., resulting in compound 11.

The saturated ring-A system with the 5α-configuration may be obtained as shown in Scheme 4. Typically, reduction with lithium in liquid ammonia, according to the procedure of Stork et al, *J. Am. Chem. Soc.*, 86, 1761 (1964), reduces the 4,5-double bond to give compound 12 from the 17β-hydroxy-4-ene-3-one 26. Reoxidation of the 17-alcohol in this and any of the other corresponding alcohols may be accomplished by conventional Jones oxidation with chromic acid in acetone at about 25° C.

Alternatively, the 5α-series may be obtained by converting the acetate of the known 19-hydroxy-5α-androstane-3,17-dione, prepared by Hauser et al., *Helv. Chim. Acta.*, 47, 1961 (1964), or its analogously prepared 18-methyl, 6-alkyl and/or 16-alkyl analogues, to a bisketal, hydrolyzing the acetate and oxidizing to the 19-aldehyde, and converting to the 10-allenyl compound by one of the procedures of Schemes 1 and 2.

SCHEME 4

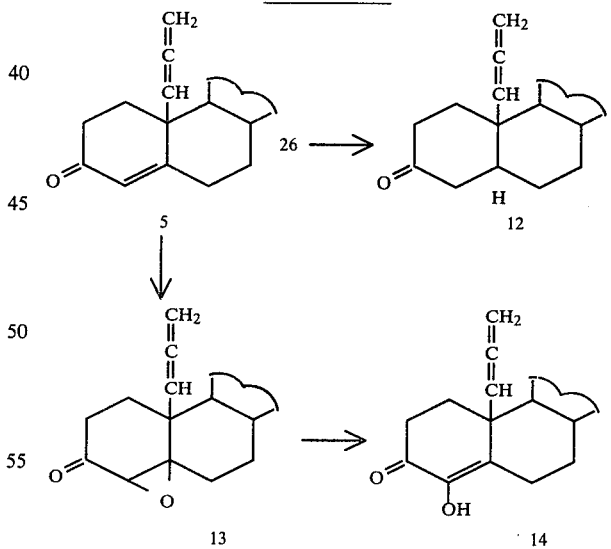

The 4-ene-3,17-dione 5 may also be converted into the 4-hydroxy derivative as shown in Scheme 4. Treatment with alkaline hydrogen peroxide to form the epoxide 13 is followed by treatment with sulfuric acid in acetic acid to open the epoxide and form the hydroxyenone 14, according to the procedure of Brodie et al, *Endocrinology*, 100, 1684 (1977).

The 5α-ketone 12 may be dehydrogenated to the 1-ene-3-one 15 as shown in Scheme 5, by reaction with dichlorodicyanoquinone in refluxing dioxane according to the procedure of Ringold et al, *Chem. and Ind.*, 211 (1962).

SCHEME 5

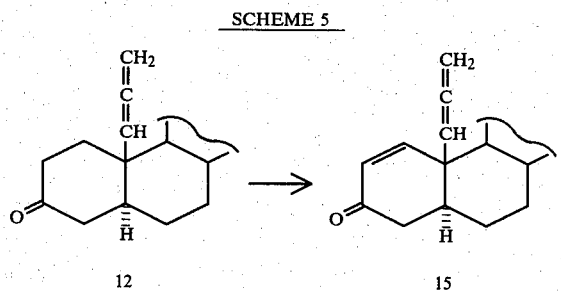

The allenyl diketal 4 may be transformed into various oxygenated derivatives according to Scheme 6.

SCHEME 6

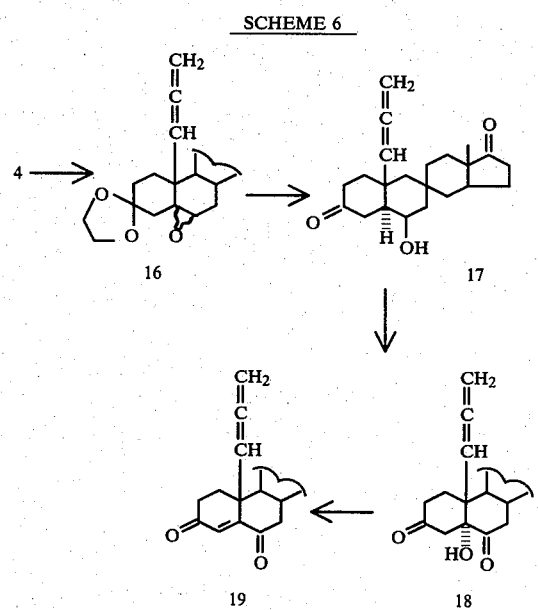

Treatment of diketal 4 with meta-chloroperbenzoic acid in dichloromethane at 0°–25° C. for 1–12 hours produces a mixture of the 5,6-epoxides 16, which may be opened to the 3,17-diketo-5,6-diol 17, using perchloric acid in aqueous THF at 25°–80° C. for 1–12 hours. The ketal groups are also removed in the process. Diol 17 is then oxidized to the 5α-hydroxy-6-ketone 18 by Jones oxidation as described hereinabove. Ketone 18 is then dehydrated to form trione 19 using p-toluenesulfonic acid in benzene or mineral acid in aqueous alcohol at 25°–70° C. for 1–4 hours.

Either the 17-alcohol 26 or its reduced 5α-analogue 12 may be alkylated at C16 by the procedure of Scheme 7.

SCHEME 7

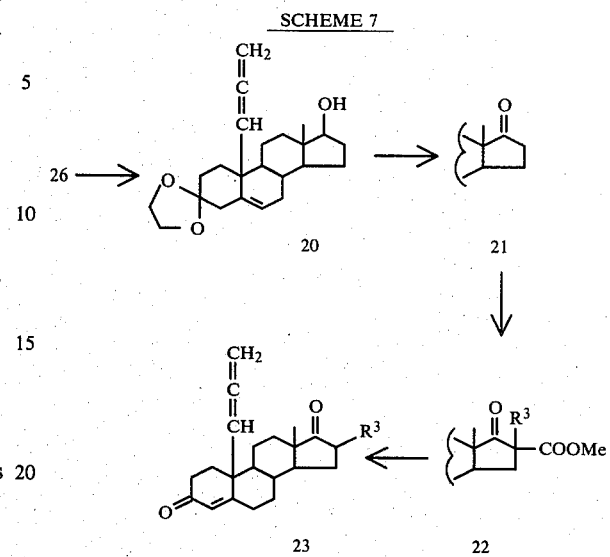

Illustrating the reaction with the 17β-alcohol 26 from borohydride reduction of compound 5, the enone is ketalized with ethylene glycol and p-toluenesulfonic acid in refluxing benzene with a water trap, to produce hydroxyketal 20. Oxidation of the 17-alcohol with chromium trioxide/pyridine complex in dichloromethane, according to the procedure of Ratcliffe et al., *J. Org. Chem.*, 35, 4000 (1970), regenerates the 17-ketone 21, which may be monoalkylated at C16 by, e.g., reaction with methyl chloroformate and potassium t-butoxide, followed by a lower alkyl halide, to form the alkylated ketoester 22. Alkaline hydrolysis, followed by acidification and warming achieves decarboxylation and deketalization to form alkylated ketone 23. The procedure of Scheme 7 may also be used to alkylate 18-methyl analogues at C16.

Alkylation at $C_6$ may be effected by the procedure of Scheme 8.

SCHEME 8

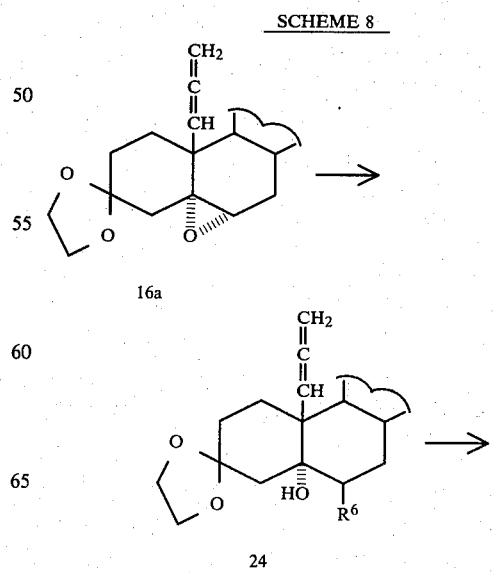

-continued
SCHEME 8

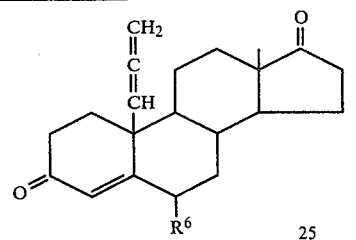

The predominant α-epoxide 16a from Scheme 6 is treated with a lower alkyl Grignard reagent in refluxing THF to produce the alkylated hydroxyketal 24. Deketalization and dehydration, under the conditions for converting compound 16 to compound 19 in Scheme 6, produce the 6-alkyl-4-ene-3,17-dione 25.

Compounds with a 7-alkyl substituent may be prepared according to Scheme 9.

SCHEME 9

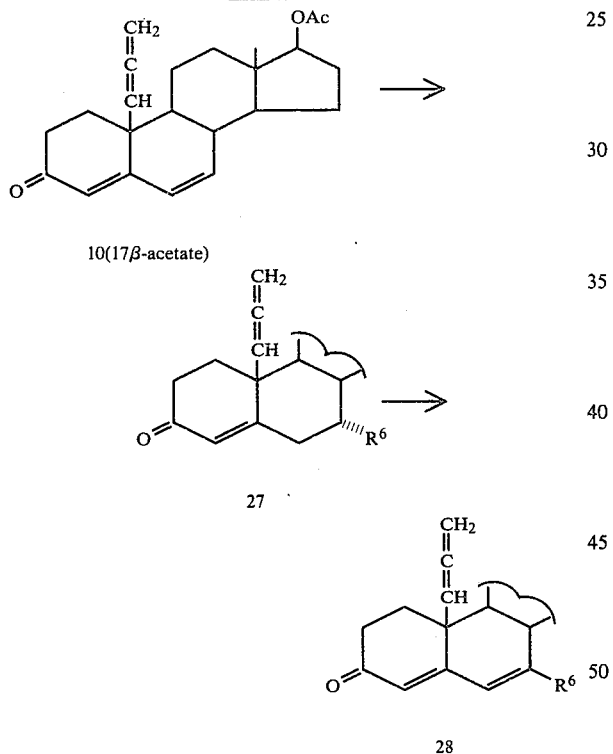

Diene 10, obtained by the procedure of Scheme 3 from compound 26, as the 17β-acetate, is reacted with lithium di(lower alkyl) copper to give the 7α-alkyl compound 27. Further dehydrogenation, following the procedure of Scheme 3 for converting enone 26 to dienone 10, converts enone 27 to dienone 28. The 7-alkyl enone 27 may be further transformed in a manner entirely analogous to enones 5 or 26.

The 18-methyl series may be prepared from the known precursor 29, prepared according to the procedure of Baddely et al, *J. Org. Chem.*, 31, 1026 (1966). The hydroxyenone 29 is converted to the 10-allenyl series as shown in Scheme 10

SCHEME 10

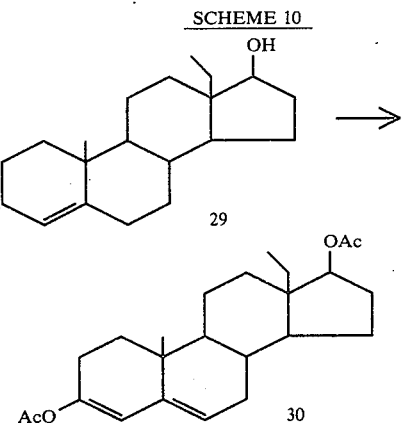

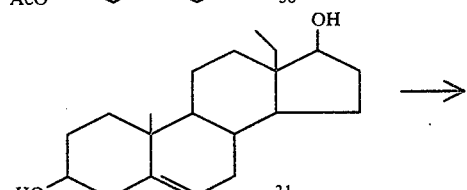

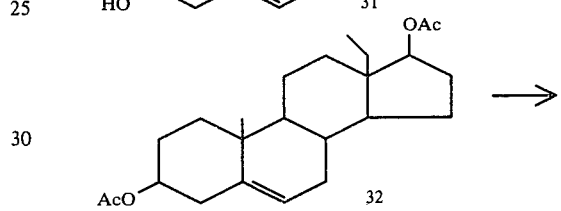

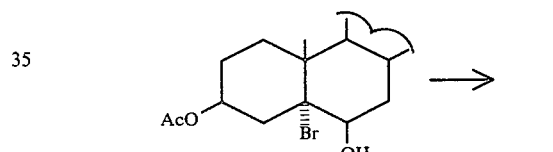

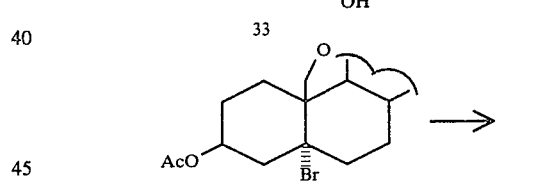

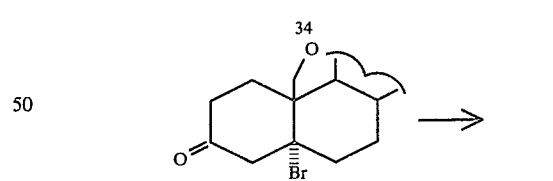

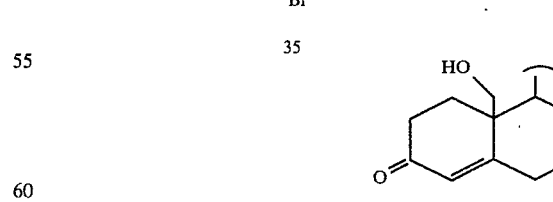

The known hydroxyenone 29 is converted to the enol diacetate 30 with isopropenyl acetate. Reduction with sodium borohydride, according to the procedure of Dauben et al, *J. Am. Chem. Soc.*, 73, 4463 (1951), produces enediol 31, which is converted to its diacetate 32 by conventional treatment with acetic anhydride and pyridine.

By analogy to the known compound with a methyl group at C13, diacetate 32 is further elaborated using the procedure of Bowers et al., *J. Am. Chem. Soc.*, 84, 3204 (1962).

The diacetate 32 is converted to bromohydrin 33 with N-bromosuccinimide. Lead tetraacetate treatment produces cyclic ether 34, which is converted to ketone 35 by hydrolysis of the acetate and oxidation. Treatment with metallic zinc effects a reductive opening of the ether and conjugation of the enone double bond, to produce the 19-hydroxy-4-ene-3-one 36. The 19-alcohol 36 may be oxidized to the aldehyde and transformed further by the procedures of the foregoing reaction Schemes.

The foregoing syntheses are illustrative, and many other conventional reactions may be used to produce or to interconvert the compounds of the invention. These conventional reactions and conditions may be found, e.g., in Fieser et al, "Steroids" (Reinhold, New York, 1959); Djerassi, Ed., "Steroid Reactions" (Holden-Day, San Francisco, 1963); Kirk et al, "Steroid Reaction Mechanisms" (Elsevier, Amsterdam et al, 1968); Carruthers, "Some Modern Methods of Organic Synthesis" (Cambridge U. Press, Cambridge, 1971); and Harrison et al, "Compendium of Organic Synthetic Methods" (Wiley-Interscience, New York et al, 1971).

The compounds of the invention have a high affinity for aromatase enzymes. In addition, the aromatase inhibitors of the invention bind to the enzyme in a time dependent manner, thereby progressively inactivating the enzyme. Accordingly, these inhibitors are effective in the treatment of conditions which are already known to respond to aromatase inhibitors, but they have a prolonged effect because of the irreversibility of their inhibitory action.

The aromatase inhibitory action of the compounds of the invention may be studied using a radioenzymatic assay. An aromatase enzyme preparation from the microsomal fraction isolated from human placenta is employed. Stereospecific elimination of $1\beta$ and $2\beta$ tritium labels from androgen substrates such as testosterone or androstenedione and the subsequent appearance of tritiated water is utilized to measure the rate of enzyme reaction during in vitro incubations.

The aromatase inhibitors are evaluated for enzyme affinity by measuring their competive inhibition of the conversion of $^3H$-testosterone to estrogens. The $1\beta,2\beta$-$^3H$-testosterone (40–60 Ci/mM specific activity) is dissolved in assay buffer to provide an assay concentration of about $1.7 \times 10^{-9}$ M with approximately 200,000 disintegrations per minute in 100 ul. Assay buffer contains 100 mM KCl, 10 mM $KH_2PO_4$, 10 mM dithiothreitol and 1 mM EDTA at pH 8.0. Inhibitor compounds (~10 mg) are dissolved in ethanol and/or dimethylsulfoxide and diluted with assay buffer to provide assay concentrations ranging from $10^{-4}$ M to $10^{-9}$ M. Tritium-labeled testosterone (substrate) 100 ul, and enzyme inhibitor, 100 ul, are added to a 35 ml centrifuge tube containing 600 ul of a NADPH generating system. Aromatase requires NADPH as a cofactor, therefore a generating system is included which uses 0.5 mM $NADP^+$, 2.5 mM glucose-6-phosphate, and 1.0 unit/ml of glucose-6-phosphate dehydrogenase in assay buffer. The enzyme reaction is started by the addition of 700 ul of aromatase preparation, usually 50 ug microsomal protein per ml of assay buffer. These preparations are mixed using a vortex mixer and incubated for 30 minutes at 37° C. with a 95% $O_2$:5% $CO_2$ gas phase in a Dubinoff shaking incubator.

The enzymatic reaction is terminated by the addition of 10 ml of $CHCl_3$. After vortexing for 20 sec., aqueous/organic emulsions are dispersed and phase separation achieved following centrifugation at 600×g for 10 min. Duplicate 500 ul samples of the upper aqueous phase of each incubation sample are added to 10×75 mm culture tubes. To these tubes, 500 ul of cold 0.25% dextran-coated charcoal suspension is added, vortexed, incubated for 15 min. at 4° C., then centrifuged at 2600×g in a refrigerated centrifuge (4° C.). The supernatant fraction is decanted into a 20 ml scintillation vial and 15 ml of aqueous scintillation cocktail is added. The radioactivity of $^3H_2O$ resulting from liberated 1 and 2 tritium atoms during the enzymatic reaction is determined by counting for 10 min. in a liquid scintillation counter. This assay procedure is adapted from the procedures of Reed et al, *J. Biol. Chem.*, 251, 1625 (1976), and Thompson et al, *J. Biol. Chem.*, 249, 5364 and 5374 (1974).

The enzymatic activity is related to the percentage of tritium liberated from $^3H$-testosterone which appears as $^3H_2O$. The activity of each concentration of inhibitor is calculated as a percentage of the vehicle control, which is arbitrarily set at 100%. The molar concentration of each inhibitor which reduces enzyme activity by 50% is called the 50% Inhibition Concentration, $IC_{50}$. These values for an inhibitor of the invention, 10-(1,2-propadienyl)estr-4-ene-3,17-dione, and the reference compounds aminoglutethimide, androsta-1,4,6-triene-3,17-dione and 1-dehydrotestololactone, are shown in Table 1. The 10-allenyl compound has greater enzyme affinity than other known inhibitors, which have been used either as antifertility agents in rodents or to block peripheral aromatization in patients with breast cancer.

TABLE 1

| Competitive Inhibition of Aromatase Inhibitors | |
|---|---|
| Inhibitor Compound | $IC_{50}$ |
| 10-(1,2-propadienyl)estr-4-ene-3,17 dione | $7.5 \times 10^{-8}$ |
| α-(p-Aminophenyl)-α-ethylglutar-imide (aminoglutethimide) | $1.0 \times 10^{-6}$ |
| Androsta-1,4,6-triene-3,17-dione | $1.0 \times 10^{-7}$ |
| 1,2,3,4,4a,4b,7,9,10,10a-Decahydra-2-hydroxy-2,4b-dimethyl-7oxo-1-phenanthrene-propionic acid O-lactone (1-dehydrotestololactone) | $2.5 \times 10^{-6}$ |

The compounds of the invention, which demonstrate good inhibition, $IC_{50} \leq 10^{-7}$ M, were evaluated for time-dependent inhibition. In this assay, the inhibitor is preincubated with the enzyme prior to assaying for enzyme activity in the presence of high substrate levels. A time-related decrease in enzyme activity is indicative of irreversible binding of the inhibitor with the enzyme.

In the time-dependent assay, an amount of the enzyme inhibitor in 100 ul of the assay buffer described above which will provide assay concentrations which are approximately one and ten times the $IC_{50}$ values are added to 35 ml centrifuge tubes containing 600 ul of the NADPH generating system described above. The preincubation is started by the addition of 700 ul of aromatase preparation, usually 500–800 ug of microsomal protein per ml of assay buffer. These preparations are mixed using a vortex mixer and incubated for 0, 10, 20 or 40 minutes at 25° C. Then 100 ul of $1\beta,2\beta$-$^3H$ testosterone is added in assay buffer to provide an assay concentration of substrate ($4.5 \times 10^{-7}$ M) which is at least ten times the Km of testosterone (0.045 uM). Following vortexing, the enzyme incubation is continued for 10 minutes before being terminated by the addition of chloroform. The amount of radioactivity in the aqueous fraction is determined by scintillation procedures. The enzymatic activity is calculated from the percent of $^3$H-testosterone converted to $^3$H$_2$O. The enzyme activity for each concentration of inhibitor at each time period of preincubation is calculated as a percent of the "0" minute vehicle control arbitrarily set at 100%. Therefore, the percent enzyme inhibition is expressed as a percentage of the 100 percent enzyme activity value.

Compounds which show time-dependent inhibition are then assayed to establish the inhibition constant, $K_i$, which is the apparent dissociation constant for the enzyme-inhibitor complex. This determination requires measurements at initial velocities of enzyme reaction. The enzyme activity is determined following different preincubation times at various inhibitor concentrations when assayed at a substrate concentration of at least ten times the Km of testosterone. The enzyme half-life ($t_{\frac{1}{2}}$) at these different inhibitor concentrations ([In]) is used to determine the $K_i$ by the linear regression equation of the $t_{\frac{1}{2}}$ vs. 1/[In]. The $K_i$ is equivalent to the inhibitor concentration when $t_{\frac{1}{2}}$ is equal to zero. The results of the time-dependent assays are shown in Table 2.

TABLE 2

Time Dependent Inhibition of Aromatase

| Inhibitor | Inhibitor Conc. (uM) | Percent Inhibition Preincubation time (minutes) | | | Apparent Ki (uM) |
|---|---|---|---|---|---|
| | | 0 | 20 | 40 | |
| 10-(1,2-prpopa- | 0.01 | 0.0 | 13.0 | 31.5 | 0.014 |
| dienyl) estr-4-ene- | 0.05 | 6.2 | 42.5 | 56.6 | |
| 3,17-dione | 0.1 | 8.6 | 45.7 | 62.4 | |
| | 0.5 | 34.7 | 62.5 | 76.5 | |
| | 1.0 | 50.2 | 69.2 | 84.0 | |
| Aminoglutheth- | 1.0 | 13.7 | 0.5 | 14.4 | 20.28 |
| imide | 10.0 | 70.0 | 64.0 | 73.2 | |
| Androsta-1,4,6- | 0.1 | 20.5 | 45.5 | 54.8 | 0.110 |
| triene-3,17-dione | 1.0 | 88.8 | 92.8 | 95.2 | |
| 1-Dehydrotestolo- | 0.25 | 0.0 | 3.6 | 36.1 | 7.9 |
| lactone | 2.5 | 24.7 | 82.7 | 96.9 | |

Table 2 shows the percent inhibition following different time periods of preincubation prior to the addition of the labeled substrate, for various concentrations of 10-(1,2-propadienyl)estrenedione and reference compounds. The allenyl compound demonstrates significant time-dependent inhibition of aromatase at very low concentrations, i.e., 0.01–0.05 uM. Based on these activities, the 10-(1,2-propadienyl)estrenedione has superior activity to known therapeutic agents used in breast cancer therapy and which also inhibit aromatase.

The $K_i$ for the 10-(1,2-propadienyl)estrenedione is $1.4 \times 10^{-8}$ M. These data indicate that this inhibitor is irreversibly bound to the enzyme with an affinity for the enzyme site which is three times greater than that of the natural substrate testosterone, which has an enzyme affinity (Km) of $4.48 \times 10^{-8}$ M. The enzyme affinity of the 10-allenyl compound exceeds the enzyme affinity of androsta-1,4,6-triene-3,17-dione by a factor of 8.1, 1-dehydrotestololactone by 58.1 and aminoglutethimide by 1,491.2.

These data demonstrate that 10-(1,2-propadienyl-)estr-4-ene-3,17-dione is superior to known aromatase inhibitors. Significant irreversible aromatase inhibition is also shown by the other compounds of the invention of Formulae I and II. Improved therapeutic efficacy and specificity is shown for these aromatase inhibitors in the treatment of estrogen dependent cancers and inhibition of estrogen-regulated reproductive processes of animals and man.

The aromatase inhibitors of the invention are useful therapeutically for the treatment of any normal or pathological condition mediated by estrogen production and responsive to inhibition of estrogen production. Such conditions include but are not limited to those discussed hereinabove, which have already been shown to respond to aromatase inhibitors. The compounds of the invention may also be used as irreversible inhibitors for aromatase enzymes in any applications where high activity and specificity are required.

In general, the compounds having either Formula I or II may be administered analogously to known aromatase inhibitors such as androsta-1,4,6-triene-3,17-dione, testololactone or aminoglutethimide. They may be administered orally or parenterally in either solid or liquid form, and in the presence of a pharmaceutically acceptable carrier if desired. Solid dosage unit forms, e.g., capsules, pills, tablets and the like are suitable. Individual solid dosage units may contain, in addition to the active ingredients, a pharmaceutically acceptable carrier, e.g., starch, sugar, sorbitol, gelatin, lubricants, silicic acid, talcum, and the like. Alternatively, liquid dosage forms for either oral administration or sterile injectable solutions are suitable for use with the present method. More than one form of administration may be used where such is found to be clinically useful.

Oral administration of the compounds of the invention, e.g., for the treatment of breast carcinoma, by capsules or tablets is advantageously effected with individual dosage units containing from 1.0 to 250 mg of the aromatase inhibitor, preferably from 10 to 50 mg. A daily dosage of from 50 to 1000 mg, preferably from 10 to 150 mg is recommended.

The compounds of Formulae I or II may also be administered as liquid suspensions or solutions using a sterile liquid, such as an oil, water, an alcohol, or mixtures thereof, with or without the addition of a pharmaceutically suitable surfactant, suspending agent, or emulsifying agent for oral or parenteral administration.

A suspension or solution for intramuscular injection will advantageously contain from 10 to 200 mg/ml of aromatase inhibitor. A solution for intravenous injection will advantageously contain from 0.1 to 10 mg/ml. Effective aromatase inhibitory dosages are from 10 to 200 mg. daily im and from 10 to 100 mg daily iv.

The active compound may also be administered by means of a sustained release system whereby the compound of Formula I or II is gradually released at a controlled, uniform rate from an inert or bioerodible carrier by means of diffusion, osmosis, or disintegration of the carrier, during the treatment period. Controlled release drug delivery systems may be in the form of a patch or bandage applied to the skin or to the buccal, sublingual or intranasal membranes, an ocular insert placed in the cul de sac of the eye, or a gradually eroding tablet or capsule or a gastrointestinal reservoir administered orally. Administration by means of such sustained release delivery systems permits the tissues of the body to be exposed constantly for a prolonged time period to a therapeutically effective dosage of a compound of Formula I or II. The unit dosage of the compound administered by means of a sustained release system will approximate the amount of an effective daily dosage multiplied by the maximum number of days during which the carrier is to remain on or in the body of the host. The sustained release carrier may be in the form of a solid or porous matrix or reservoir and may be formed from one or more natural or synthetic polymers, including modifid or unmodified cellulose, starch, gelatin, collagen, rubber, polyolefins, polyamides, polyacrylates, polyalcohols, polyethers, polyesters, polyurethanes, polysulphones, polysiloxanes and polyimides and mixtures, laminae, and copolymers thereof. The compound of Formula I or II may be incorporated in the sustained release carrier in a pure form or may be dissolved in any suitable liquid or solid vehicle, including the polymer of which the sustained release carrier is formed.

Examples of suitable dosage forms are given hereinbelow, although the invention is not limited in any way by the examples chosen, since these modes of administration are generally known to the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of 10-(1,2-propadienyl)estr-4-ene-3,17-dione(5)

3,17-Bis(ethylenedioxy)-19-ethynylandrost-5-ene-19-ol 2 (Covey et al, Tet. Let. 2105 (1979)), (1.8 g, 4.4 mMole) in pyridine (20 ml) is cooled to 0° C., then treated with methanesulfonyl chloride (700 mg, 6 mMole). The mixture is kept at $-20°$ C. for 48 hours, then diluted with ether and washed with 1 N HCl, saturated $NaHCO_3$, and brine, the dried and concentrated.

The resultant crude mesylate 3 is dissolved in toluene (50 ml) and cooled to $-70°$ C., then treated with sodium bis(methoxyethoxy)aluminum hydride (2 ml, 70% in benzene) and allowed to stand for 12 hours at $-20°$ C. Water is then carefully added and the mixture extracted with ether. The ether solution is washed with 1 N HCl, and aqueous $NaHCO_3$, then dried and concentrated to afford a residue, which is purified by chromatography on silica gel in ethyl acetate/hexane to give allene 4.

The allene 4 is dissolved in acetone (30 ml), p-toluenesulfonic acid (50 mg) is added, and the solution stirred overnight at room temperature, then concentrated. The residue is taken up in ether, washed with aq. $NaHCO_3$, dried, concentrated and chromatographed on silica gel. The product diketone is further purified by recrystallization from hexane to afford the product 5 as colorless crystals, m.p. 104°–105° C.

By a completely analogous procedure, 18-methyl and 16-alkyl analogues may be converted to the corresponding allenyl ketones.

EXAMPLE 2

Preparation of 10-(1,2-propadienyl)estr-4-ene-3-one-17β-ol(26)

Diketone 5 (312 mg, 1 mMole) in absolute methanol (10 ml) is treated with $NaBH_4$ (15 mg) for 1 hour at 0° C. Acetic acid (1 drop) is then added and the mixture evaporated to dryness. The residue is taken up in ether, washed with 1 N HCl, and brine, then dried and evaporated. The crude product is recrystallized from methanol to afford the 17β-alcohol 26.

Using the foregoing procedure, analogous substituted diketones may be selectively reduced at C17 to produce the analogous alcohols. The 17α-alcohols may be prepared by conventional processes, e.g., by inversion via the 17β-tosylate, displacement with acetate, and hydrolysis.

EXAMPLE 3

Preparation of 10-(1,2-propadienyl)estra-1,4-diene-3,17-dione (9)

To a solution of 150 mg diketone 5 in 16 ml of t-butyl alcohol and 0.7 ml of glacial acetic acid is added 150 mg of selenium dioxide. The mixture is heated under reflux for 20 hours, then cooled and diluted with ethyl acetate. The solution is filtered, the filtrate washed with 1 N NaOH, 1 N $H_2SO_4$, and brine, then dried and concentrated. The residue is chromatographed on silica gel with ethyl acetate/hexane to afford the product 9.

EXAMPLE 4

Preparation of 10-(1,2-propadienyl)estra-4,6-diene-3,17-dione (10)

A mixture of diketone 5 (250 mg) and chloranil (460 mg) in t-butyl alcohol (17 ml) is heated at reflux for 3 hours. The mixture is diluted with ethyl acetate and filtered. The filtrate is washed with 1 N NaOH and brine, then dried and concentrated. Chromatography of the residue on silica gel using ethyl acetate/hexane affords the product 10, which is recrystallized from dichloromethane/hexane, m.p. 152°–154° C.

EXAMPLE 5

Preparation of 10-(1,2-propadienyl)estra-1,4,6-triene-3,17-dione (11)

A mixture of 400 mg of diketone 5, 1.40 g of chloranil and 15 ml of sec-amyl alcohol is heated at reflux for 3 hours. On cooling, the mixture is diluted with ethyl acetate, filtered, and the filtrate washed with 1 N NaOH and brine, then concentrated. The residue is chromatographed on silica gel to afford the triene product 11.

EXAMPLE 6

Preparation of 17β-hydroxy-10-(1,2-propadienyl)-5α-estran-3-one(12)

The 17β-alcohol 26 (312 mg, 1 mMole) in THF (5 ml) is added to lithium (21 mg, 3 mMole) in ammonia (20 ml) containing t-butanol (80 mg) at $-70°$ C. After 10 min at $-70°$ C., the reaction is treated with solid ammonium chloride, the ammonia allowed to evaporate, the residue dissolved in ether, and the ether solution washed with brine, dried and evaporated. The residue is recrystallized from methanol to afford the product 12.

EXAMPLE 7

Preparation of 4-hydroxy-10-(1,2-propadienyl)estr-4-ene-3,17-dione(14)

To diketone 5 (650 mg) in methanol (5 ml) at 15° C., is added hydrogen peroxide (0.6 ml of 30% H$_2$O$_2$). A solution of sodium hydroxide (46 mg in water, 0.4 ml) is added dropwise. After 1 hour at 15° C., the solution is stirred for 2 hours at 25° C., then poured into brine and extracted with ether. The ether solution is dried and concentrated, and the residue recrystallized from methanol to afford the epoxide 13. The crude epoxide is added to acetic acid (5 ml) containing conc. sulfuric acid (0.1 ml) and the mixture stirred at 25° C. for 4 hours, then poured onto ice. The solid is filtered off and recrystallized from ethyl acetate to afford the product 14.

EXAMPLE 8

Preparation of 10-(1,2-propadienyl)-5α-estr-1-ene-3,17-dione (15)

A mixture of 5α-diketone 12 (200 mg) and dicyanodichloroquinone (320 mg) in dioxane (4 ml) is heated at reflux for 24 hours. The residue is diluted with ethyl acetate and washed with 1 N NaOH and brine, then dried and concentrated. Chromatography of the residue on silica gel using ethyl acetate/hexane affords the product 15.

EXAMPLE 9

Preparation of 5α-hydroxy-10-(1,2-propadienyl)estra-3,6,17-trione (18)

m-Chloroperbenzoic acid (85 mg. of 85% reagent, 0.42 mMole) is added to bisketal-5-ene 4 (152 mg., 0.38 mMole) in methylene chloride (7 ml) at 0° C. The mixture is maintained at 0° C. for 16 hours then diluted with methylene chloride and washed with water, 10% sodium carbonate, brine then dried and evaporated. The residue, together with a similar residue obtained in a separate reaction starting from bisketal-5-ene 4 (52 mg), is subjected to flash chromatography on silica gel in 60% ethyl acetate/hexane to afford α-epoxide 16a (126 mg., 59%) and β-epoxide (16b (24 mg., 11%). The 5,6-α-epoxide 16a (126 mg., 0.30 mMole) in THF (20 ml) and water (5 ml) is treated with 8 drops of 70% perchloric acid and stirred at 25° C. for 48 hours, when the absence of epoxide is shown by thin layer chromatography. The mixture is diluted with ether, washed with aq. Na$_2$CO$_3$ and brine, then dried (MgSO$_4$) and concentrated to afford crude diol 17 (95 mg). The crude diol in acetone (25 ml) at 0° C. is treated dropwise with Jones' reagent until a brown color persists for 15 mins. The mixture is then partitioned between methylene chloride and water. The organic phase is washed with brine, then dried and concentrated to afford ketol 18 as an oil.

EXAMPLE 10

Preparation of 10-(1,2-propadienyl)estr-4-ene-3,6,17-trione (19)

Ketol 18 (80 mg) is dissolved in benzene (50 ml), p-toluenesulfonic acid (15 mg) is added and the mixture heated at reflux for 30 mins. using a Dean-Stark water separator. The cooled solution is then washed with aq. Na$_2$CO$_3$ and brine, then dried and evaporated. The residue is recrystallized from dichloromethane/hexane to afford trione 19, m.p. 187°–190° C.

EXAMPLE 11

Preparation of 3,17-bis(ethylenedioxy)-10-(1,2-propadienyl)estr-5-ene (4)

Propargylic alcohol 2 (3.3 g., 8 mMole) is treated with pyridine (10 ml) and acetic anhydride (10 ml) for 16 hours at 25°. The solvents are then removed under reduced pressure and the residue dissolved in ether, washed with 1 N HCl, aq. NaHCO$_3$, dried (MgSO$_4$) and concentrated. The residue is dried well under vacuum to give crude acetate 6. n-Butyllithium (33 ml of a 2.1 M solution, 70 mMole) is added to a slurry of 1-pentynyl copper (9.2 g., 70 mMole) in ether (150 ml) maintained at −40° C. and stirred mechanically. The mixture is maintained at −40° C. for 1 hour then cooled to −70° and the crude acetate 6 in ether (20 ml) is added. After 6 minutes at −70°, methanol (2 ml) followed by aqueous NH$_4$Cl is added. The mixture is diluted with ether, filtered through Celite, the ether phase is then washed with 1 N HCl, aq. NaHCO$_3$, dried and concentrated. The residue is flash chromatographed over silica gel using 25% ethyl acetate/hexane and recrystallized from dichloromethane/pentane, to afford the allenyl-bisketal 4, m.p. 113°–114° C.

EXAMPLE 12

Preparation of 17β-acetoxy-7α-methyl-10-(1,2-propadienyl)estr-4-en-3-one (27)

Diene 10, prepared from alcohol 26 by the procedure of Example 4, is converted to its 17-acetate by the procedure of Example 11. The crude acetate (352 mg, 1 mMole) in ether (2 ml) is added to an ethereal solution of lithium dimethylcopper prepared from 300 mg (2 mMole) of cuprous iodide and 2 ml (4 mMole) of a 2 M solution of methyl lithium in ether (5 ml) at −30° C. After 1 hour, the solution is allowed to warm to 0° C., then poured into water and extracted with ether. The combined ethereal extracts are washed with brine, then dried and evaporated. Recrystallization from ethyl acetate/hexane yields the product 27.

The 7α-methyl compound 27 is converted to the 4,6-diene by dehydrogenation with chloranil, using the procedure of Example 4.

EXAMPLE 13

Tablet Formulation

An illustrative tablet formulation suitable for use in making up the aromatase inhibitor composition of the invention and suitable for use in treating estrogen-mediated conditions is as follows. The proportions are designed for administration to a patient weighing about 80 kg in a regimen wherein administration is thrice daily.

| | | |
|---|---|---|
| (a) 10-(1,2-Propadienyl)estr-4-ene-3,17-dione | | 10 g |
| (b) Wheat starch | | 50 g |
| (c) Lactose | | 150 g |
| (d) Magnesium stearate | | 8 g |

A granulation obtained upon mixing the lactose with a portion of the starch and a granulated starch paste made from the remainder of the starch is dried, screened, and mixed with the active ingredients (a) and (b) and the magnesium stearate. The mixture is compressed into 1000 tablets each weighing 218 mg.

EXAMPLE 14

IM Injectable Formulations

Illustrative IM injectable compositions suitable for use in the method of the invention are as follows.

A. Oil Type:

| | |
|---|---|
| 10-(1,2-Propadienyl)estr-4-ene-3,17-dione | 10 mg |
| Butylated hydroxyanisole | 0.01% w/v |
| Butylated hydroxytoluene | 0.01% w/v |
| Peanut Oil or Sesame Oil sufficient to make | 1.0 ml |

B. Suspension Type:

| | |
|---|---|
| 10-(1,2-Propadienyl)estr-4-ene-3,17-dione | 10 mg |
| Sodium Carboxymethylcellulose | 0.5% w/v |
| Sodium Bisulfite | 0.02% w/v |
| Water for injection, sufficient to make | 1.0 ml |

The preceding examples can be repeated with similar success by substituting the generically or specifically prescribed reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compounds having the formulae

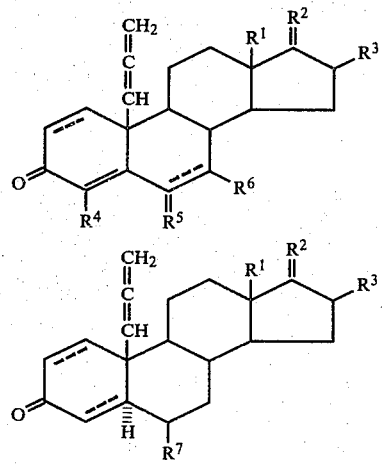

wherein $===$ represents a single or a double bond; $R^1$ is $CH_3$ or $C_2H_5$; $R^2$ is (H)($OR^8$) or O; $R^3$ is H or $C_{1-3}$ alkyl; $R^4$ is H or $OR^8$; $R^5$ is $H_2$, O or (H)($C_{1-3}$ alkyl); $R^6$ and $R^7$ are each independently H or $C_{1-3}$ alkyl; and $R^8$ is H or $C_{1-4}$ alkanoyl.

2. The compounds of claim 1, wherein $R^1$ is methyl.

3. The compounds of claim 1, wherein $R^2$ is (H) (OH) or O.

4. The compounds of claim 1 having formula I wherein $R^4$ is H or acetoxy.

5. The compounds of claim 1, wherein $R^3$ is H.

6. The compounds of claim 1, wherein $===$ is a single bond.

7. The compounds of claim 1 having Formula I wherein $R^5$ is $H_2$.

8. The compounds of claim 1 having Formula I, wherein $R^1$ is methyl; $R^2$ is O; $R^3$, $R^4$ and $R^6$ are each H; and $R^5$ is $H_2$.

9. 10-(1,2-Propadienyl)estr-4-ene-3,17-dione, a compound of claim 1.

10. 10-(1,2-Propadienyl)estra-1,4,6-triene-3,17-dione, a compound of claim 1.

11. 4-Acetoxy-10-(1,2-propadienyl)estr-4-ene-3,17-dione, a compound of claim 1.

12. 10-(1,2-propadienyl)estra-1,4-diene-3,17-dione, a compound of claim 1.

13. 17β-Hydroxy-10-(1,2-propadienyl)estr-4-ene-3-one, a compound of claim 1.

14. 17β-Hydroxy-10-(1,2-propadienyl)-5α-estran-3-one, a compound of claim 1.

15. 10-(1,2-Propadienyl)-5α-estrane-3,17-dione, a compound of claim 1.

16. 10-(1,2-Propadienyl)estra-4,6-diene-3,17-dione, a compound of claim 1.

17. 10-(1,2-Propadienyl)-5α-estr-1-ene-3,17-dione, a compound of claim 1.

18. 4-Hydroxy-10-(1,2-propadienyl)estr-4-ene-3,17-dione, a compound of claim 1.

19. 10-(1,2-Propadienyl)estr-4-ene-3,6,17-trione, a compound of claim 1.

20. Compound having the formulae

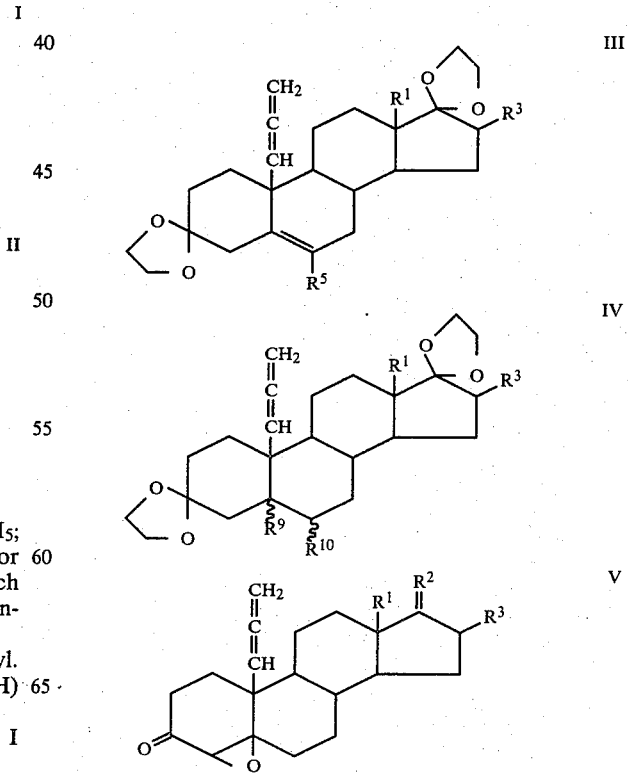

-continued

VI

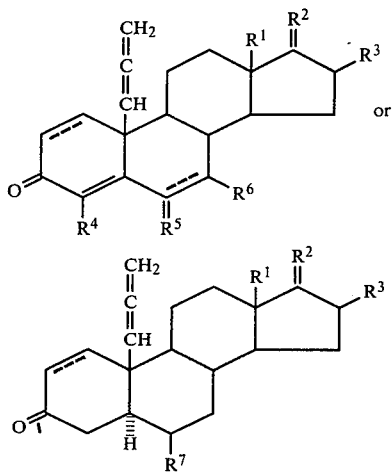

wherein $R^1$ is $CH_3$ or $C_2H_5$; $R^2$ is (H) ($OR^8$) or O; $R^3$ is H or $C_{1-3}$ alkyl; $R^5$ is H, or $C_{1-3}$ alkyl; $R^8$ is H or $C_{1-4}$ alkanoyl; $R^9$ and $R^{10}$ together are >O, or $R^9$ is OH and $R^{10}$ is $C_{1-3}$ alkyl; and $R^{11}$ is (H)(OH) or O.

21. A method of irreversibly inhibiting aromatase activity, which comprises contacting an aromatase enzyme with an effective inhibiting amount of a compound of claim 1.

22. A method of treating a normal or pathological condition mediated by estrogen production and responsive to inhibition of estrogen production, which comprises administering to a subject having said condition a therapeutically effective aromatase inhibiting amount of a compound of claim 1.

23. A pharmaceutical composition comprising a compound having the formula

I or

II wherein ----
represents a single or a double bond; $R^1$ is $CH_3$ or $C_2H_5$; $R^2$ is (H) ($OR^8$) or O; $R^3$ is H or $C_{1-3}$ alkyl; $R^4$ is H or $OR^8$; $R^5$ is $H_2$, O or (H) ($C_{1-3}$ alkyl); $R^6$ and $R^7$ are each independently H or $C_{1-3}$ alkyl; and $R^8$ is H or $C_{1-4}$ alkanoyl; and a pharmaceutically acceptable carrier.

* * * * *

UNITED STATES PATENT AND TRADEMARK OFFICE
CERTIFICATE OF CORRECTION

PATENT NO. : 4,289,762

DATED : September 15, 1981

INVENTOR(S) : Brian W. Metcalf and J. O'Neal Johnston

It is certified that error appears in the above-identified patent and that said Letters Patent are hereby corrected as shown below:

Column 9, lines 26-33, the right-hand formula should appear as follows:

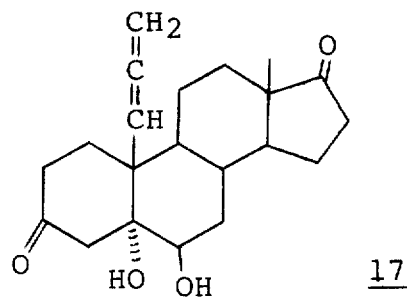

Column 12, lines 41-53, the formulas should appear as follows:

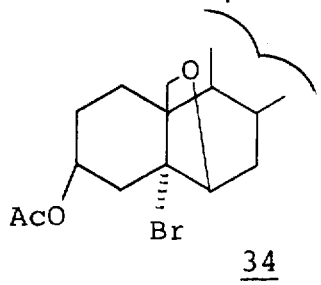 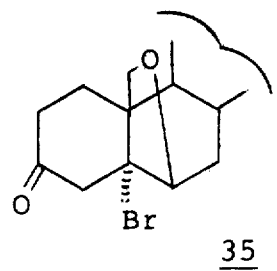

UNITED STATES PATENT AND TRADEMARK OFFICE
CERTIFICATE OF CORRECTION

PATENT NO. : 4,289,762

DATED : September 15, 1981

INVENTOR(S) : Brian W. Metcalf and J. O'Neal Johnston

It is certified that error appears in the above-identified patent and that said Letters Patent are hereby corrected as shown below:

Column 21, lines 48-55 (Claim 1), the formula should appear as follows:

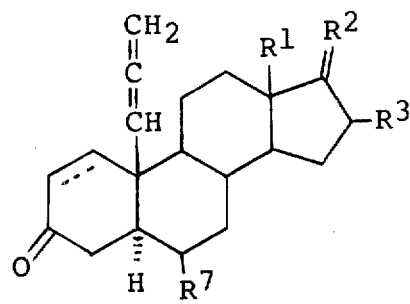

II

Signed and Sealed this

First Day of November 1983

[SEAL]

Attest:

Attesting Officer

GERALD J. MOSSINGHOFF

Commissioner of Patents and Trademarks